United States Patent
Hahn et al.

(10) Patent No.: US 11,793,762 B2
(45) Date of Patent: Oct. 24, 2023

(54) COMPOSITION AND METHOD FOR REDUCING JOINT PAIN ASSOCIATED WITH HEMARTHROSIS AND HEMOPHILIC ARTHROPATHY

(71) Applicant: UPEXMED CO. LTD., Anyang-si (KR)

(72) Inventors: Soonkap Hahn, Irvine, CA (US); Gantumur Battogtokh, Incheon (KR); Oyuntuya Gotov, Incheon (KR); Gil Man Kim, Anyang (KR); Min Hyo Seo, Daejeon (KR)

( * ) Notice: Subject to any disclaimer, the term of this patent is extended or adjusted under 35 U.S.C. 154(b) by 90 days.

(21) Appl. No.: 16/940,759

(22) Filed: Jul. 28, 2020

(65) Prior Publication Data

US 2020/0352869 A1    Nov. 12, 2020

Related U.S. Application Data

(63) Continuation-in-part of application No. PCT/IB2019/000335, filed on Apr. 5, 2019.

(60) Provisional application No. 62/653,476, filed on Apr. 5, 2018.

(51) Int. Cl.
| | |
|---|---|
| *A61K 9/50* | (2006.01) |
| *A61P 19/02* | (2006.01) |
| *A61K 9/00* | (2006.01) |
| *A61K 31/341* | (2006.01) |
| *A61K 31/415* | (2006.01) |

(52) U.S. Cl.
CPC .......... *A61K 9/5015* (2013.01); *A61K 9/0019* (2013.01); *A61K 31/341* (2013.01); *A61K 31/415* (2013.01); *A61P 19/02* (2018.01)

(58) Field of Classification Search
CPC .. A61K 9/5015; A61K 9/0019; A61K 31/341; A61K 31/415; A61K 9/0021; A61K 31/365; A61K 9/5031; A61K 31/42; A61K 31/444; A61P 19/02; A61P 29/00
See application file for complete search history.

(56) References Cited

U.S. PATENT DOCUMENTS

2006/0122150 A1*   6/2006   Argentieri ............ A61K 9/0019
                                                           514/54

FOREIGN PATENT DOCUMENTS

CN           104208014 A    * 12/2014

OTHER PUBLICATIONS

Rattray, B.; Nugent, D.; Young, G. Celecoxib in the treatment of haemophilic synovitis, target joints, and pain in adults and children with haemophilia. Haemophilia, 12(5): 514-517. (Year: 2006).*
Gentile, P.; Chiono, V.; Carmagnola, I.; Hatton, P. An overview of poly(lactic-co-glycolic) acid (PLGA)-based biomaterials for bone tissue engineering. Int. J. Mol. Sci. 15(3): 3640-3659. (Year: 2014).*
"International Search Report," Patent Cooperation Treaty, dated Aug. 28, 2019.

* cited by examiner

*Primary Examiner* — Jessica Worsham
(74) *Attorney, Agent, or Firm* — CIONCA IP Law P.C.; Marin Cionca (57) ABSTRACT

The invention disclosed herein relates to a composition and method of reducing the joint pain associated with hemarthrosis or hemophilic arthropathy. The method includes administering a COX-2 inhibitor, such as rofecoxib, celecoxib, valdecoxib, etoricoxib or other "coxib" drug which is encapsulated in PLGA micro-particles. The COX-2 inhibitor can be administered directly to an area where pain exists by an injection device. In a preferred embodiment, rofecoxib or celecoxib can be encapsulated in PLGA micro-particles for controlled, sustained release over a 2-8-week period. The non-systemic delivery and the controlled, sustained release of rofecoxib alleviate the cardiovascular side effects associated with systemic rofecoxib treatments.

7 Claims, 5 Drawing Sheets

COMPOSITION AND METHOD FOR REDUCING JOINT PAIN ASSOCIATED WITH HEMARTHROSIS AND HEMOPHILIC ARTHROPATHY

CROSS-REFERENCE TO RELATED APPLICATIONS

This application is a continuation-in-part of PCT/IB2019/000335 (formerly PCT/US19/26053) filed on Apr. 5, 2019, which claims the benefit of U.S. Provisional Application No. 62/653,476 filed Apr. 5, 2018, both applications being hereby incorporated by reference, to the extent that they are not conflicting with the present application.

BACKGROUND OF INVENTION

1. Field of the Invention

The invention relates to compositions and methods for treating joint pain associated with hemarthrosis and hemophilic arthropathy.

2. Description of the Related Art

Hemarthrosis is a bleeding into joints and a common problem for subjects that suffer from hemophilia. Joint bleeding accounts for 70-80% of all bleeding cases in patients with severe hemophilia and causes extreme pain. It can repeat to a cycle of bleeding, synovitis, and more bleeding, which gradually destructs the joints (i.e., hemophilic arthropathy). Pain in one or more joints is a common problem in up to two-thirds of patients with severe hemophilia. Pain is therefore a critical aspect of hemophilia and adds to the burden of the disease. Unfortunately, there is no pain management treatment currently available for hemarthrosis and hemophilic arthropathy that is effective and FDA approved specifically for such ailments. To control the severe pain, some hemophilic patients use opioids, which expose them to the risk of addiction. Therefore, there is a strong need for a new and improved medication and treatment method that is effective in treating the pain associated with hemarthrosis and hemophilic arthropathy experienced by hemophilic subjects.

Non-steroidal anti-inflammatory drugs (NSAIDs) inhibit cyclo-oxygenase (COX) which converts arachidonic acids to prostaglandins. Prostaglandins are produced in response to injury or infection and cause inflammation, which is associated with the symptoms of redness, swelling, pain and fever. Two isozymes, COX-1 and COX-2, are found in humans. Traditional NSAIDs inhibit both COX-1 and COX-2 enzymes. However, their use is associated with the side effects such as gastrointestinal and renal toxicity. The anti-inflammatory action of NSAIDs and reduction of pain are produced by the inhibition of COX-2 activity, while the undesired side effects are caused by the inhibition of COX-1 activity. Thus, it was thought that inhibitors more selective to COX-2 ("COX-2 inhibitors") would have reduced side effects.

Indeed, some of COX-2 inhibitors such as rofecoxib is proven clinically to reduce the side effects of the traditional NSAIDs. However, when systemically administered, which is typical, most COX-2 inhibitors, including rofecoxib, cause adverse cardiovascular side effects (e.g., rofecoxib appears to alter the balance of vasoactive eicosanoids [prostacyclin and thromboxane] and to suppress the inflammatory mediators implicated in the progression of atherogenesis and ischemic myocardial injury). The adverse cardiovascular side effects led to withdrawal of COX-2 inhibitors from the U.S. market, except celecoxib. However, celecoxib is also not recommended for a long-term use due to the adverse cardiovascular side effects.

Most NSAIDs including COX-2 inhibitors are taken orally and are thus subject to systemic exposure. As already stated, the systemic exposure of COX-2 inhibitors has been shown to cause adverse cardiovascular side effects.

Attempts were made to address the above side effects, but the solutions provided have shortcomings. For example, in order to minimize the systemic exposure of COX-2 inhibitors, R. R. Lala et al. delivered topically COX-2 inhibitors such as etoricoxib using nanoemulsion-based gel formulations (Appl. Nanosci., 143-151, 2014). This method appears to reduce the systemic exposure of etoricoxib. However, this method utilizes a passive diffusion mechanism across the skin which may deliver inconsistent amount of etoricoxib.

J. Baek et al. co-encapsulated two traditional NSAIDs of ibuprofen and naproxen and one COX-2 inhibitor of celecoxib into polylactic acid (PLA) and polylactic glycolic acid (PLGA) microcapsules, which were taken orally (Drug Design, Development and Therapy, 1707-1717, 2017). This complex sustained and controlled delivery system aimed mainly to reduce the gastrointestinal problem. To further minimize the gastrointestinal problem, they added cimetidine, an anti-acid, into the microcapsules. However, this oral route of administration will not reduce the adverse cardiovascular side effects.

M. R. Santos et al. prepared a traditional NSAID of naproxen, a COX-2 inhibitor of celecoxib and a matrix metalloproteinase inhibitor (MMP inhibitor) of cipemastat encapsulated in PLA micro-particles (Osteoarthritis and Cartilage, S232, 2008). They suspended these PLA micro-particles in hylan G-F 20 and injected it into joints of guinea pigs and rabbits. Although they apparently demonstrated that the local injection of pain management drugs encapsulated in PLA minimizes the systemic exposure, their overall system in G-F 20 is too viscous to inject effectively. In addition, it is not clear that their system's sustained and controlled release of encapsulated drugs is due to PLA or hylan G-F 20. Further, this formulation, by using a plurality of drugs, increases the toxicity to the patient.

More importantly, it should be noted that none of the above prior attempts aimed to treat the pain associated with hemarthrosis or hemophilic arthropathy, so their effectiveness for these ailments is at best unknown.

Additional attempts, that appeared to have aimed at treating pain associated with hemarthrosis or hemophilic arthropathy in hemophilia patients, came out short as well. For example, Rodriguez-Merchan (Haemophilia, 20, e222-e242 (2014)) carried out a clinical trial testing celecoxib orally for 30 patients and control for 30 patients with hemophilia A and painful advanced hemophilic arthropathy (HA). The trial had been conducted for 2 months and the results apparently showed that the joint pain in the celecoxib group improved significantly as compared to the control group. Rattray (Haemophilia, 12, 514-517 (2006)) conducted a clinical trial with twelve hemophilia patients given oral celecoxib treatment. The results claimed that celecoxib was safe and effective in treating chronic synovitis and joint pain. While, these two human clinical trials appear to have demonstrated that celecoxib taken orally had positive effects on reducing pain associated with hemarthrosis or hemophilic arthropathy, their treatments' potential cardiovascular side effects of long-term oral use, which are serious as described above, were not monitored and established. Thus, these treatments are likely to expose the hemophilia patients to the serious cardiovascular harms.

Thus, there is a need to address and solve the problems associated with the prior art described above, by providing an effective and safe treatment for pain associated with hemarthrosis or hemophilic arthropathy experienced by hemophilia patients.

The aspects or the problems and the associated solutions presented in this section could be or could have been pursued; they are not necessarily approaches that have been previously conceived or pursued. Therefore, unless otherwise indicated, it should not be assumed that any of the approaches presented in this section qualify as prior art merely by virtue of their presence in this section of the application.

BRIEF INVENTION SUMMARY

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

In an aspect, a COX-2 inhibitor encapsulated in PLGA microsphere (COX-2 inhibitor PLGA MS) is suspended in non-viscous aqueous solution (COX-2 inhibitor PLGA MS solution). The aqueous solution allows for easier dispersion of the PLGA particles therein. The COX-2 inhibitor PLGA MS solution is administered locally where pain exists, through a user-friendly syringe or conventional hypodermic syringe. This simple, convenient drug delivery system limits the amount of COX-2 inhibitor exposed to the systemic circulation and thus minimizes the adverse cardiovascular side effects while reducing the joint pain associated with hemarthrosis or hemophilic arthropathy. This is a key benefit of the invention disclosed herein and was confirmed by two animal tests, pharmacokinetic (PK) test and efficacy test.

In another aspect, a method of reducing the joint pain associated with hemarthrosis is disclosed. The method includes administering a COX-2 inhibitor, such as rofecoxib, celecoxib, valdecoxib, etoricoxib or other "coxib" drug, which is encapsulated in PLGA micro-particles. The COX-2 inhibitor can be administered to an area where pain exists by a commercial painless micro-needle injection device. In a preferred embodiment, rofecoxib or celecoxib can be encapsulated in PLGA micro-particles for controlled, sustained release over a 2-8-week period. In a more preferred embodiment the sustained release target period is 14-28 days (2-4 weeks). The non-systemic delivery of and controlled, sustained release of rofecoxib or celecoxib significantly decreases the cardiovascular side effects associated with systemic rofecoxib or celecoxib treatments (e.g., oral administration).

In another aspect, the treatment for the pain associated with hemarthrosis or hemophilic arthropathy disclosed herein allows safe and effective use of drugs that were once banned or withdrawn from the market for safety reasons.

In another aspect, the treatment for the pain associated with hemarthrosis or hemophilic arthropathy disclosed herein can be used for a long time without the cardiovascular risks.

In another aspect, the treatment for the pain associated with hemarthrosis or hemophilic arthropathy disclosed herein is simple, using one drug only, yet effective, while avoiding additional systemic toxicity associated with using multiple drugs.

The above aspects or examples and advantages, as well as other aspects or examples and advantages, will become apparent from the ensuing description.

BRIEF DESCRIPTION OF THE DRAWINGS

For exemplification purposes, and not for limitation purposes, aspects, embodiments or examples of the invention are illustrated in the figures of the accompanying drawings, in which.

DETAILED DESCRIPTION

What follows is a description of various aspects, embodiments and/or examples in which the invention may be practiced. The aspects, embodiments and/or examples described herein are presented for exemplification purposes, and not for limitation purposes. It should be understood that structural and/or logical modifications could be made by someone of ordinary skills in the art without departing from the scope of the invention. Therefore, the scope of the invention is defined by the accompanying claims and their equivalents.

It should be understood that, for clarity of the specification, some or all details about some compounds or steps that are known in the art are not shown or described if they are not necessary for the invention to be understood by one of ordinary skills in the art.

It should be noted that several notations will be used herein that one of ordinary skills in the art would understand. For example, PLGA 50:50/30 kDa means PLGA having 50% PLA and 50% PGA by molar ratio and the PLGA having a molecular weight of 30,000 Daltons.

Local controlled, sustained drug delivery system (DDS) using biodegradable polymers has been actively developed since sutures made of biodegradable polymers were successfully commercialized about 40 years ago. Among all the biodegradable polymers, polylactic glycolic acid (PLGA) has shown the most potential as a drug delivery system due to its long clinical history and versatile degradation property. A number of drug delivery systems based on PLGA have been already commercialized. There are many additional PLGA-based drug delivery system products under development.

Drug release rate from PLGA micro-particles can be controlled by adjusting a number of parameters such as 1) ratio between polylactic acid (PLA) and polyglycolic acid (PGA), 2) molecular weight, 3) size of micro-particle, 4)

amount and nature of encapsulated medication and 5) end group of PLGA. In PLGA, polylactic acid (PLA) is more hydrophobic compared to polyglycolic acid (PGA) and subsequently hydrolyzes (i.e., degrades) slower. For example, PLGA 50:50 (i.e., PLA is 50% and PGA is 50%, by molar ratio) exhibits a faster degradation than PLGA 75:25 due to preferential degradation of glycolic acid proportion, if the two PLGA polymers have the same molecular weight (MW). Faster degradation of PLGA means faster release of the encapsulated drug.

Figure 1:
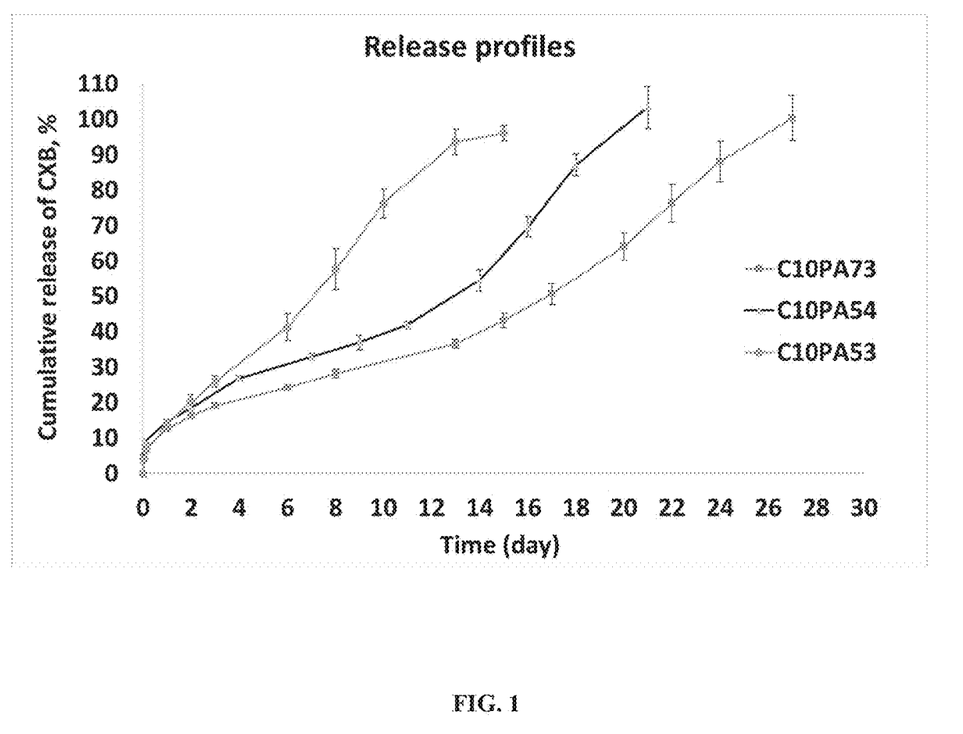
FIG. 1 illustrates in vitro release profile of celecoxib (CXB)-loaded PLGA microspheres (MS) (50:50/30 kDa, 50:50/40 kDa and 75:25/30 kDa), according to an aspect.

FIG. 1 shows that celecoxib (CXB) releases faster from PLGA 50:50 microspheres (14 days) than PLGA 75:25 microspheres (28 days) when the two PLGA polymers have the same MW of 30 kDa. PLGA with higher MW exhibits a slower degradation rate than PLGA with lower MW. Molecular weight has a direct relationship with the polymer chain size. Higher MW PLGA has longer polymer chain and requires more time to degrade than lower MW PLGA. In addition, an increase in molecular weight decreases drug diffusion rate and therefore drug release rate. FIG. 1 shows that CXB releases faster from PLGA microspheres with MW=30 kDa (14 days) than those with MW=40 kDa (21 days). For comparison, the release profiles of CXB from various PLGA microspheres are shown below in Table 1 (Characteristics of CXB-PLGA-MS prepared from different molecular weight PLGA polymer).

| Name of Microsphere | Yield (%) | EE (%) | LC (%) | Size (μm) | Release |
|---|---|---|---|---|---|
| 50:50/30 kDa | 76.5 ± 4.6 | 73.2 ± 9.2 | 7.32 ± 0.9 | 20-50 | 14 day |
| 75:25/30 kDa | 65.9 ± 3.5 | 83.2 ± 2.8 | 8.3 ± 0.2 | 25-35 | 28 day |
| 50:50/40 kDa | 75.1 ± 5.1 | 80.1 ± 0.9 | 8.01 ± 0.2 | 25-37 | 21 day |

The size of micro-particle also affects the rate of drug release. As the size of micro-particle decreases, the ratio of surface area to volume of the micro-particle increases. Thus, for a given rate of drug diffusion, the rate of drug release from the micro-particle will increase with decreasing micro-particle size. In addition, water penetration into smaller micro-particle may be quicker due to the shorter distance from the surface to the center of the micro-particle.

Further, the nature and amount of medication included in the microparticle can also affect the rate of drug release. For example, a more hydrophobic drug everolimus, encapsulated in PLGA 50:50 (30 kDa), was released over almost 1 (one) month. Celecoxib encapsulated in the same PLGA was released over 14 days, as shown in Table 1 and FIG. 1.

Lastly, the end group of PLGA has a significant effect on the release rate of drug. The ester end group makes PLGA more hydrophobic and subsequently slower release of drug compared to the hydrophilic carboxyl group.

All of the above five factors are preferably used to control the drug release of the medication disclosed herein for effective and safe treatment of pain associated with hemarthrosis or hemophilic arthropathy, as described in more detail hereinafter.

Medications

The invention disclosed herein uses COX-2 inhibitors such as rofecoxib, celecoxib, valdecoxib, etoricoxib or other "coxib" drugs. In a preferred embodiment, only one COX-2 inhibitor is used, which either rofecoxib or celecoxib.

Celecoxib is a non-steroidal anti-inflammatory drug (NSAID) used in the treatment of osteoarthritis, rheumatoid arthritis, acute pain, painful menstruation and menstrual symptoms, and to reduce numbers of colon and rectum polyps in patients with familial adenomatous polyposis. It is very hydrophobic molecule with 4.3 mg/ml solubility in water. Celecoxib can be taken orally 100-200 mg twice per day. A highly selective reversible inhibitor of the COX-2 isoform of cyclooxygenase, celecoxib inhibits the transformation of arachidonic acid to prostaglandin precursors. Therefore, it has analgesic and anti-inflammatory properties. COX-2 is extensively expressed in cells involved in inflammation and is upregulated by bacterial lipopolysaccharides, cytokines, growth factors, and tumor promoters. Celecoxib is approximately 10-20 times more selective for COX-2 inhibition over COX-1. It binds with its polar sulfonamide side chain to a hydrophilic side pocket region close to the active COX-2 binding site. In theory, this selectivity allows celecoxib and other COX-2 inhibitors to reduce inflammation (and pain) while minimizing gastrointestinal adverse drug interactions (e.g. stomach ulcers) that are common with nonselective NSAIDs.

Rofecoxib is also a COX-2 selective inhibitor. Once, it was a very popular pain medication. However, it was withdrawn from the market in 2004 due to numerous deaths caused by cardiovascular side effects. As stated hereinbefore, celecoxib is also not recommended for a long-term use due to the adverse cardiovascular side effects. However, in spite of their known cardiovascular risks, these two medications can now be safely and effectively used, according to the invention disclosed herein.

Micro-Particles

Micro-particles represent an attractive means to achieve the desired local delivery of pain management medications, including for treating joint pain associated with hemarthrosis or hemophilic arthropathy, as described herein. Micro-particles used herein refer to particles having sizes between 1 μm and 250 μm, preferably less than 100 μm and include microcapsules, microspheres and other particles. Micro-particles composed of drugs or medicaments and polymers are commonly used as a sustained, controlled release drug delivery system. Microcapsules generally have a drug core coated with a polymer film and may be spherical or non-spherical in shape. In contrast, microspheres have drugs dispersed evenly in polymer and are spherical in shape.

The composition of PLGA can consist of equal to or more than 50% of polylactic acid (PLA). In some embodiments, each PLGA micro-particle contains 1-50% of a COX-2 inhibitor by weight. Again, drug release rate from each PLGA micro-particles can be controlled by adjusting a number of parameters such as 1) ratio between polylactic acid (PLA) and polyglycolic acid (PGA), 2) molecular weight, 3) size of micro-particle, 4) amount and nature of encapsulated medication and 5) end group of PLGA. To further adjust their drug release rates, some PLGA microsphere may contain excipients such as polyethylene glycol (PEG) or polyvinylpyrrolidone (PVP) which can accelerate the biodegradation of micro-particles.

For the microparticles disclosed herein, the preferred molecular weight of PLGA is between 10,000 and 150,000 Daltons, and more preferably between 25,000 and 75,000 Daltons.

Micro-Particle Fabrication

Micro-particles in the present invention can be prepared by microencapsulation, spray drying, precipitation, hot melt microencapsulation, co-extrusion, precision particle fabrication (PPF) or other fabrication techniques. Microencapsulation techniques use single, double or multiple emulsion process in combination with solvent removal step such as evaporation, extraction or coacervation step. They are the most commonly used techniques to prepare micro-particles.

The above techniques including the microencapsulation techniques can be used for water soluble drug, organic solvent soluble drug and solid powder drug. Polyesters including PLGA can be processed with any one of the above techniques.

Figure 2A:
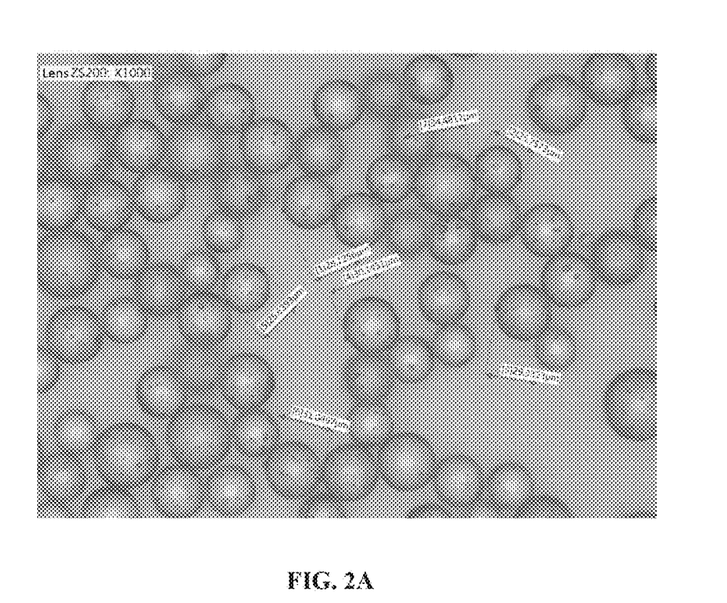
FIGS. 2A-B illustrate the size of CXB-PLGA-MS by optical microscope and particle size analyzer, respectively, according to an aspect.
Figure 2B:
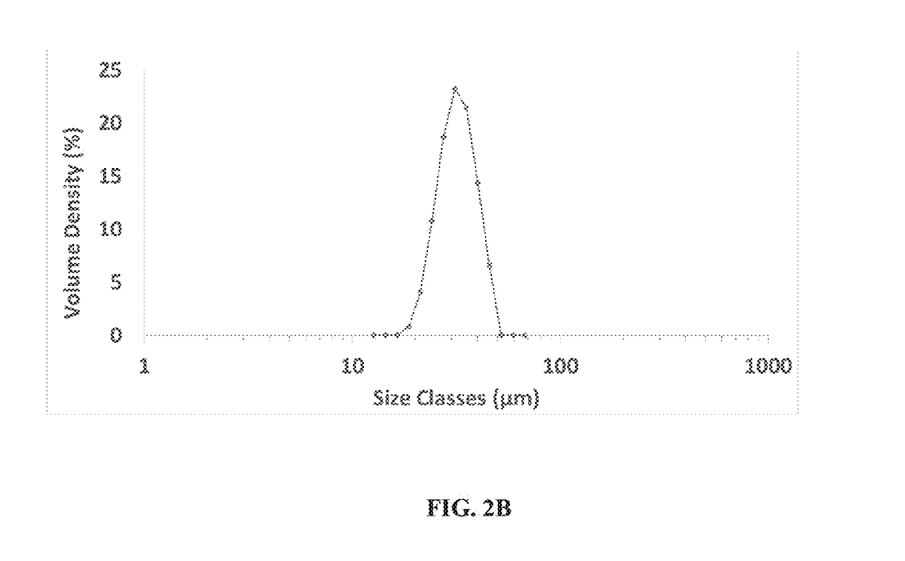

In an aspect, the present invention used a SPG (Shirasu Porous Glass) membrane machine manufactured by MCTech. This machine pressed oil solution or emulsified solution (water-in-oil) through ceramic membrane (pore size of 5-30 µm, preferred pore size is 20 µm) using nitrogen gas into the continuous phase tank filled with 1.5% polyvinyl alcohol solution to prepare microspheres. The use of MCTech machine with the SPG membrane produces relatively uniform size of microspheres compared to conventional methods using a homogenizer with a propeller stirrer. The uniform and small size (e.g., 50 µm) of microsphere shown in FIG. 2 is important for injecting intraarticularly without clogging. The inventors found that 22G and 23G needles are adequate for injecting the microspheres with 20-50 µm size.

Examples

Preparation of Celecoxib-Loaded PLGA Microsphere

PLGA (1 g; MW=30 kDa, PLA:PGA=50:50) was dissolved in 9 mL of dichloromethane (DCM) by stirring at room temperature for 1 h. To the polymer solution, celecoxib (100 mg, CXB) was added and stirred for additional 10 min. The solution (oil phase) was poured to the dispersion phase tank of SPG (Shirasu Porous Glass with 20 µm pore size) membrane machine manufactured by MCTech and pressed through the SPG membrane using nitrogen gas into the continuous phase tank filled with 1.5% polyvinyl alcohol solution. The process is being carried out for around 2 hours. The aqueous phase was collected in a glass beaker and stirred with propeller stirrer for 12 hours at room temperature to remove DCM. Then, cold DI water (500 mL) was added to the microsphere solution and filtered on 20 µm filter paper or centrifuged at 3000 rpm for 5 min after cooling down for 6 h at 4° C., followed by washing with cold water (1 L). The collected pellets were freeze-dried for 24-48 h and vacuum dried for 72-96 h at 39° C. in vacuum oven. The resulting microspheres shown in FIG. 2 were analyzed to have 20-50 µm size (mean size of 34.1 µm measured by particle size analyzer) and a spherical morphology observed by optical microscope. In order to calculate the drug encapsulation efficiency (EE) and drug loading efficiency (LC), certain amount of CXB-PLGA MS was weighed and dissolved in acetonitrile via 10 min-sonication. The resulting solution was diluted with a mobile phase consisting of acetonitrile and 0.1% phosphoric acid solution at ratio of 60:40 and measured by HPLC. The drug encapsulation efficiency (EE) and drug loading content (LC) were calculated by the following equations:

$$EE\ (\%) = \frac{\text{Weight of found } CXB}{\text{Weight of feed } CXB} \times 100$$

$$LC\ (\%) = \frac{\text{Weight of found } CXB}{\text{Weight of feed } CXB + \text{Feed } PLGA} \times 100$$

The average EE and LC from 3 runs are shown in Table 1 above.

In Vitro Release Study

The in vitro release study was carried out by sample-and-separate method. Briefly, 5 mg of microsphere sample (n=3) was taken in 100 mL flask and dispersed in 50 mL of release medium (0.5% Tween 20 and 0.1% sodium azide in PBS at pH 7.4). The flasks were placed in orbital agitating incubator at 37° C. and shaken at 100 rpm. At certain time points, 40 mL medium was taken and centrifuged at 3,000 rpm for 2 min. From the supernatant, 30 mL was pipetted and replaced by same amount of the fresh media. In the collected supernatant, the content of the released CXB was analyzed by HPLC. The CXB release profiles of CXB-PLGA microspheres (50:50 with MW=30 kDa and 40 kDa and 75:25 with MW=30 kDa) are measured and shown in FIG. 1.

Pharmacokinetic Study in Beagle Dog

Pharmacokinetic (PK) study was carried out using ten months old male beagle dogs (n=3). The beagle dogs were fasted for 24 h. CXB-PLGA microsphere (MS) sample (50:50/30 kDa) was suspended in the diluent (0.9% of sodium chloride, 0.5% of carboxy methyl cellulose sodium (CMC) and 0.1% of polysorbate 80). Then, 1 mL of the suspended solution of microsphere (1.5 mg/kg dose) was injected into the knee in hind legs of beagle dog intraarticularly. Synovial fluid sample of 50 µL from the treated joints were aspirated at 0, 1, 3, 7, 11, and 14 days after the injection. The synovial fluid was centrifuged, and the supernatant was stored at −80° C. until CXB content determination. Blood sample of 3 mL from the jugular vein was collected into tubes containing K2 EDTA as anticoagulant at 0, 3 h, 8 h, 1, 3, 7, 11, and 14 days after the injection and spun down for 5 min at 3000 rpm to produce plasma. The plasma samples were used for CXB content determination. CXB concentration in plasma and synovial fluid was analyzed by LC-MS method (shown in FIGS. 3A and 3B, respectively).

Figure 3A:
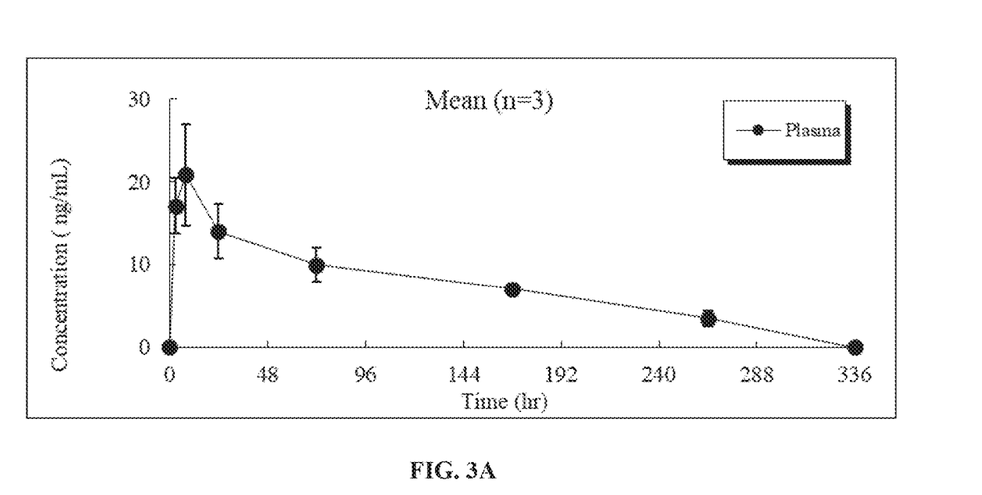
FIG. 3A illustrates beagle pharmacokinetic (PK) profile in plasma post intraarticular administration of CXB-PLGA MS (50:50/30 kDa), according to an aspect.
Figure 3B:
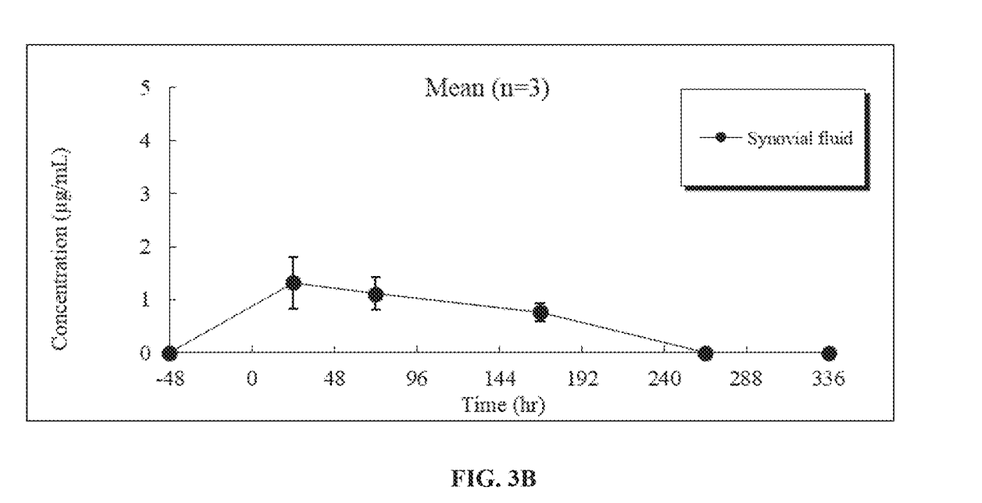
FIG. 3B illustrates beagle PK profile in synovial fluid post intraarticular administration of CXB-PLGA MS (50:50/30 kDa), according to an aspect.

As shown in FIG. 3A, Cmax of CXB in plasma post intraarticular (i.a.) administration of 1.5 mg/kg of CXB-PLGA MS was found to be 20.8 ng/mL (see Table 2 below), which is 17 times lower than that in human plasma after oral administration (200 mg/day) [Int J Bioanal Methods Bioequival Study, 2(2), 34-40].

TABLE 2

Main parameters value of PK data in plasma post intraarticular administration of CXB-PLGA-MS (50:50/30 kDa) to beagle dog

|  | AUC (last) | AUC(inf) | Cmax (ng/mL) | Tmax | CL(inf)/F | Vz(terminal)/F | t1/2 | AUC, % |
|---|---|---|---|---|---|---|---|---|
| 1 | 1896.7 | 2421.4 | 14.3 | 8.0 | 0.006 | 1.1 | 127.5 | 21.6 |
| 2 | 2601.7 | 3579.1 | 26.5 | 8.0 | 0.004 | 0.9 | 151.3 | 27.3 |
| 3 | 2396.9 | 2896.7 | 21.6 | 8.0 | 0.005 | 0.8 | 110.6 | 17.2 |
| Mean | 2298.4 | 2965.7 | 20.8 | 8.0 | 0.005 | 0.9 | 129.8 | 22.1 |
| SD | 362.6 | 581.95 | 6.1 | 0.0 | 0.00 | 0.1 | 20.4 | 5.0 |

In case of PK of synovial fluid (FIG. 3B), Cmax of 1,360 ng/mL was 71.6-fold higher than that in serum plasma post i.a. administration of same formulation (see Tables 2 and 3). This result confirmed that very little amount of CXB enters the systemic circulation post i.a. administration of CXB-PLGA MS formulation. These results indicate that CXB-PLGA MS could exhibit much lower systemic toxicity post i.a. administration as compared with free CXB after oral administration.

TABLE 3

Main parameters value of PK data in synovial fluid post intraarticular administration of CXB-PLGA-MS (50:50/30 kDa) to beagle dog

|   | AUC (last) | AUC (inf) | Cmax (μg/mL) | Tmax | CL(inf)/F | Vz(terminal)/F | t1/2 | AUC (%) |
|---|---|---|---|---|---|---|---|---|
| 1 | 132.5 | 224.1 | 1.0 | 72.0 | 0.06 | 10.8 | 112.7 | 40.9 |
| 2 | 210.9 | 353.5 | 1.8 | 24.0 | 0.04 | 7.4 | 120.8 | 40.3 |
| 3 | 150.1 | — | 1.2 | 24.0 | — | — | — | — |
| Mean | 164.5 | 288.8 | 1.4 | 40.0 | 0.05 | 9.1 | 116.8 | 40.6 |
| SD | 41.2 | 91.5 | 0.4 | 27.7 | 0.02 | 2.5 | 5.7 | 0.4 |

—: Not available

Also, the Cmax post i.a. administration to the beagle dog was 1.7-4 times greater than that in human synovial fluid after oral administration at 200 mg (3.3 mg/kg) dosage for 5 days, indicating high local delivery dose potential of the polymeric microsphere formulation to the articular area. Since the therapeutic effect of CXB for an inflammation and pain reduction has been proved by previous studies [Rodriguez-Merchan and Rattray], it is believed that this formulation has high efficacy against the pain associated with hemarthrosis or hemophilia arthropathy. In both PK profiles, CXB was detected till 11 days after administration, indicating that the release of CXB from the microsphere formulation is similar to the in vitro release behavior of the formulation (FIG. 1).

Efficacy Study in Rat Hemophilic Arthropathy (HA) Model

Figure 4:
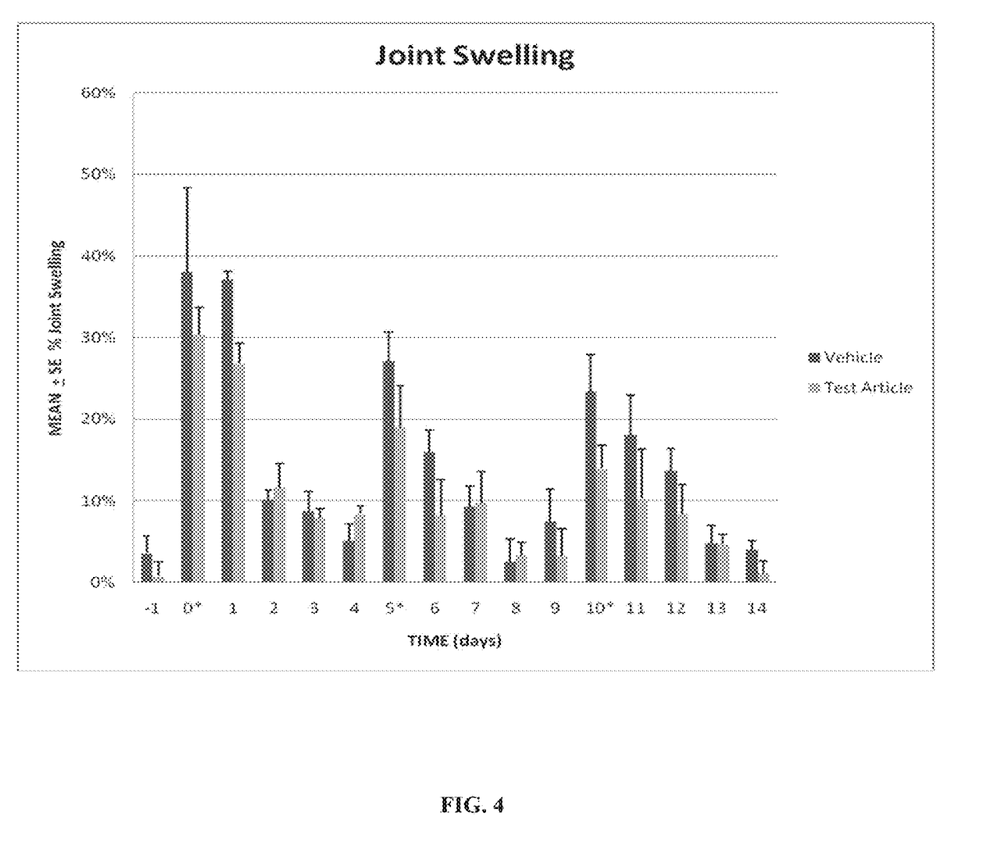
FIG. 4 illustrates percent of joint swelling (±SEM) per study day, for vehicle and test article treated groups.

Two groups of 6 rats each were treated with either Vehicle (100 μL of diluent) or Test Article (100 μL of CXB-PLGA MS, 50:50/30 kDa) on Day 0 via an intraarticular injection to the hind left knee joint. The in-life study was conducted over a period of 16 days (Days −1, 0 and 1 through 14). Induced hemophilic arthropathy (HA) was achieved via injection of autologous whole blood to the left hind knee joint of each animal. The HA induction was done on three separate occasions on Day 0, Day 5 and Day 10. Animals were assessed daily for in life effects on joint swelling and Gait score over a period of 16 study days. The % change in joint size was determined by calculating the difference in knee size between the HA induced left knee and the contralateral naïve right knee of each animal. Joint size was determined by measuring the longitudinal (L) and transverse (T) axes of the knee with a digital caliper. The oval area (OA) of each knee was calculated as follows: $OA = L \times T \times 3.14 \times 0.25$. The percent change of joint swelling (% S) was calculated as follows: % S=(OA left knee−OA right knee)/OA right knee×100%. The results of joint swelling measurement are shown in FIG. 4, which illustrates percent of joint swelling (±SEM) per study day, for vehicle and test article treated groups. Joint measurements on days 0, 5 and 10 were taken 4 hours post HA induction.

Joint swelling values for the Test Article treated group are consistently lower than those of the Vehicle treated group for 12 of the 15 days post first HA induction (Day 0). Notably the joint swelling for the Test Article is lower on each of the three HA Induction Days (Day 0, 5 and 10) at 4 hours post induction. The swelling is also lower for the Test article treated group at 24 hours post HA induction for each of the three HA induction events. A likely indication that the test article was having a beneficial effect on joint swelling as compared to the Vehicle treated group. Joint swelling is also lower for the later days of the study, Days 8 through 14, indicating that the beneficial effect may be sustained from the initial dosing on Day 0, out to a total of 14 days when the study was terminated.

Figure 5:
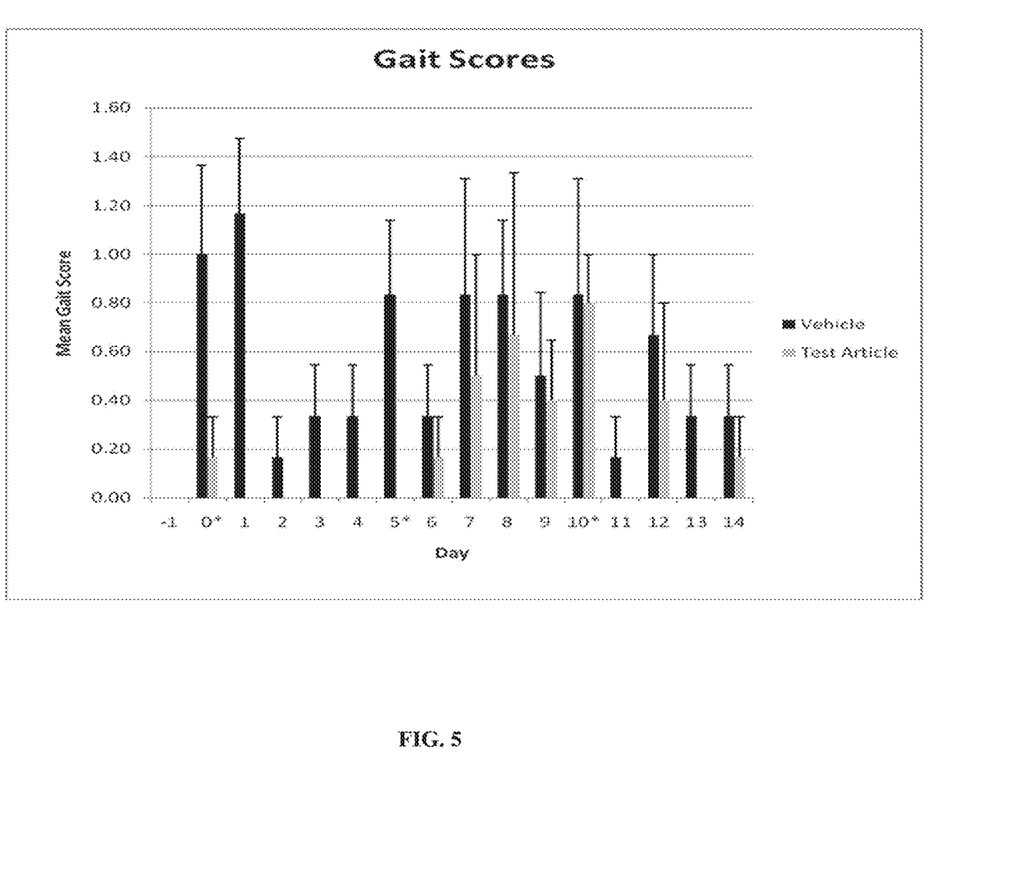
FIG. 5 illustrates gait scores (±SEM) per study day, for vehicle and test article treated groups.

The Gait score of each animal was determined on a daily basis using the foot prints of each animal taken by staining the hind limbs and recoding the foot prints on paper sheets. A scoring scheme of 0 to 4 was used to denote gait status with 0=normal, 1=slight limp, 2=limp, 3=dragging, or 4=carrying. Gait scores are consistently lower for the Test Article treated group than for the Vehicle treated group. The lower Gait scores are observed on each of the three HA induction days (Day 0, 5 and 10). The lower Gait scores are also observed 24 hours post each of the three HA induction on (Days 1, 6 and 11). Gait scores are consistently lower for the Test Article treated groups vs the Vehicle treated group, indicating that the beneficial effect may be sustained from the initial dosing on Day 0 out to a total of 14 days when study was terminated. The results of gait score is shown in FIG. 5, which shows gait scores (±SEM) per study day for vehicle and test article treated groups. Gait scores on Days 0, 5 and 10 were taken 4 hours post HA induction.

Excipients

Micro-particles in the present invention may also contain one or more pharmaceutically acceptable additives. The term "additive" is all components contained in micro-particles other than drugs or polymer and includes, but not limited to, buffers, preservatives and antimicrobials. It can also include hydrophilic materials such as polyethylene glycol (PEG) or polyvinylpyrrolidone (PVP) which can accelerate the biodegradation of micro-particles.

Painless Microinjection Device

Conventional hypodermic needles are often used in clinical practice to deliver medications across the skin into the bloodstream. Injections with hypodermic needles are important from a clinical standpoint, but painful. The present invention may require injections at multiple sites. Painless micro-needle injection device such as ClickSoft™ Microinjection Device by PKA SoftTouch Corp. and patch such as Microneedle Drug Delivery System by 3M have been developed and commercialized. The present invention can use one of these new injection methods to inject at single site or multiple sites.

Again, in a preferred embodiment, rofecoxib or celecoxib can be encapsulated in PLGA micro-particles for controlled, sustained release over a 2-8-week period. The non-systemic delivery of and controlled, sustained release of rofecoxib or celecoxib significantly decreases the cardiovascular side effects associated with systemic rofecoxib or celecoxib treatments (e.g., oral administration). In a more preferred embodiment the sustained release target period is 14-28 days. Longer periods than 28 days would increase the risk of not being able to address any unexpected reactions or issues the patient may experience due to the drug. Shorter release periods than 14 days would require the subject to be injected too often.

It may be advantageous to set forth definitions of certain words and phrases used in this patent document. The term "or" is inclusive, meaning and/or. The phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like.

Further, as used in this application, "plurality" means two or more. A "set" of items may include one or more of such items. Whether in the written description or the claims, the terms "comprising," "including," "carrying," "having," "containing," "involving," and the like are to be understood to be open-ended, i.e., to mean including but not limited to. Only the transitional phrases "consisting of" and "consisting essentially of," respectively, are closed or semi-closed transitional phrases with respect to claims.

Throughout this description, the aspects, embodiments or examples shown should be considered as exemplars, rather than limitations on the apparatus or procedures disclosed or claimed. Although some of the examples may involve specific combinations of method acts or system elements, it should be understood that those acts and those elements may be combined in other ways to accomplish the same objectives.

Acts, elements and features discussed only in connection with one aspect, embodiment or example are not intended to be excluded from a similar role(s) in other aspects, embodiments or examples.

If any presented, the claims directed to a method and/or process should not be limited to the performance of their steps in the order written, and one skilled in the art can readily appreciate that the sequences may be varied and still remain within the spirit and scope of the present invention.

Although aspects, embodiments and/or examples have been illustrated and described herein, someone of ordinary skills in the art will easily detect alternate of the same and/or equivalent variations, which may be capable of achieving the same results, and which may be substituted for the aspects, embodiments and/or examples illustrated and described herein, without departing from the scope of the invention. Therefore, the scope of this application is intended to cover such alternate aspects, embodiments and/or examples. Hence, the scope of the invention is defined by the accompanying claims and their equivalents. Further, each and every claim is incorporated as further disclosure into the specification.

What is claimed is:

1. A method to reduce cardiovascular risks and systemic toxicity while treating pain associated with hemarthrosis or hemophilic arthropathy in a human, the method comprising administering an intraarticular injection of a plurality of micro-particles directly into the site of the pain associated with hemarthrosis or hemophilic arthropathy, the plurality of micro-particles comprising a composition of PLGA and a single COX-2 inhibitor, wherein the COX-2 inhibitor is celecoxib, wherein the PLGA encapsulates the COX-2 inhibitor;
   wherein the composition comprises 7.32-50% COX-2 inhibitor by weight;
   wherein the micro-particles have a size between 20-50 µm;
   wherein the PLGA has 50% PLA and 50% PGA by molar ratio and a molecular weight of 30,000 Daltons; and
   wherein the COX-2 inhibitor has a sustained release period of 14 to 28 days.

2. A method of treating pain associated with hemarthrosis or hemophilic arthropathy comprising:
   receiving a plurality of micro-particles, the plurality of micro-particles comprising a composition of PLGA and a single COX-2 inhibitor;
   filling an injection device with the plurality of micro-particles, and
   reducing cardiovascular risks and systemic toxicity by administering an intraarticular injection of the plurality of micro-particles directly into the site of the pain associated with hemarthrosis or hemophilic arthropathy of a human,
   wherein the COX-2 inhibitor is celecoxib;
   wherein the composition comprises 7.32-50% COX-2 inhibitor by weight;
   wherein the PLGA has 50% PLA and 50% PGA, or 75% PLA and 25% PGA by molar ratio; and wherein the COX-2 inhibitor has a sustained release period of 14 to 28 days.

3. The method of treating pain associated with hemarthrosis or hemophilic arthropathy as recited in claim 2, wherein the micro-particles have a size between 1 µm and 100 µm.

4. The method of treating pain associated with hemarthrosis or hemophilic arthropathy as recited in claim 2, wherein the pain site comprises a human joint.

5. The method of claim 2, wherein the PLGA has 50% PLA and 50% PGA by molar ratio, and has a molecular weight of 30,000 Daltons, and wherein the micro-particles have a size between 20 µm and 50 µm.

6. The method of claim 2, wherein the PLGA has 50% PLA and 50% PGA by molar ratio and a molecular weight of 40,000 Daltons, and wherein the micro-particles have a size between 20 µm and 50 µm.

7. The method of claim 2, wherein the PLGA has 75% PLA and 25% PGA by molar ratio and a molecular weight of 30,000 Daltons, and wherein the micro-particles have a size between 20 µm and 50 µm.

* * * * *